(12) United States Patent
Lampropoulos et al.

(10) Patent No.: US 11,116,597 B2
(45) Date of Patent: Sep. 14, 2021

(54) BIOPSY DEVICE SUPPORT OR HOLDER AND METHOD OF USE

(71) Applicant: Merit Medical Systems, Inc., South Jordan, UT (US)

(72) Inventors: Justin Lampropoulos, Lehi, UT (US); Gregory R. McArthur, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 171 days.

(21) Appl. No.: 15/191,713

(22) Filed: Jun. 24, 2016

(65) Prior Publication Data

US 2017/0000578 A1 Jan. 5, 2017

Related U.S. Application Data

(60) Provisional application No. 62/186,867, filed on Jun. 30, 2015.

(51) Int. Cl.
| | |
|---|---|
| *A61B 50/26* | (2016.01) |
| *A61B 10/02* | (2006.01) |
| *F16M 11/40* | (2006.01) |
| *F16M 11/14* | (2006.01) |
| *F16M 13/02* | (2006.01) |
| *A61B 90/50* | (2016.01) |

(Continued)

(52) U.S. Cl.
CPC .......... *A61B 50/26* (2016.02); *A61B 10/0266* (2013.01); *A61B 50/20* (2016.02); *A61B 90/50* (2016.02); *F16M 11/041* (2013.01); *F16M 11/14* (2013.01); *F16M 11/40* (2013.01); *F16M 13/022* (2013.01); *A61B 2010/0208* (2013.01)

(58) Field of Classification Search
CPC ......... A61B 50/26; A61B 50/20; A61B 90/50; A61B 10/0266; A61B 2010/0208; F16M 11/041; F16M 13/022; F16M 11/40; F16M 11/14
See application file for complete search history.

(56) References Cited

U.S. PATENT DOCUMENTS

| | | | |
|---|---|---|---|
| 3,529,797 A | 9/1970 | Street | |
| 3,757,363 A * | 9/1973 | Langlais | A47C 21/003 248/314 |

(Continued)

FOREIGN PATENT DOCUMENTS

| | | |
|---|---|---|
| CN | 3166457 | 2/2011 |
| CN | 103919577 | 7/2014 |

(Continued)

OTHER PUBLICATIONS

International Search Report and Written Opinion dated Oct. 5, 2016 for PCT/US2016/039181.
European Search Report dated Jan. 25, 2019 for EP16818506.4.

*Primary Examiner* — Rene T Towa
(74) *Attorney, Agent, or Firm* — Stoel Rives LLP

(57) ABSTRACT

A support or holder for a biopsy device is disclosed. The support includes a holder section that grasps or otherwise supports the biopsy device, wherein the support may be configured with flexible support members that may be bent, flexed or articulated thereby allowing the practitioner to manipulate the support for re-positioning the biopsy device into a desired position where the biopsy device may then be actuated to acquire a tissue sample.

15 Claims, 6 Drawing Sheets

(51) Int. Cl.
*F16M 11/04* (2006.01)
*A61B 50/20* (2016.01)

(56) References Cited

U.S. PATENT DOCUMENTS

| | | | |
|---|---|---|---|
| 3,858,578 A | 1/1975 | Milo | |
| 4,867,404 A | 9/1989 | Harrington et al. | |
| 5,033,528 A * | 7/1991 | Volcani | A45B 17/00 |
| | | | 160/351 |
| 5,441,042 A | 8/1995 | Putnam | |
| 5,647,373 A | 7/1997 | Paltieli | |
| 6,085,749 A * | 7/2000 | Wardle | A61B 90/50 |
| | | | 128/845 |
| 6,086,600 A | 7/2000 | Kortenback | |
| 6,245,028 B1 | 6/2001 | Furst et al. | |
| 6,464,648 B1 | 10/2002 | Nakamura | |
| 6,610,009 B2 | 8/2003 | Person | |
| 6,758,809 B2 | 7/2004 | Briscoe et al. | |
| 7,798,452 B1 * | 9/2010 | Wessells | F16M 11/10 |
| | | | 248/163.1 |
| 8,317,695 B2 | 11/2012 | Spence et al. | |
| 2004/0230133 A1 * | 11/2004 | Miller | A61B 10/0275 |
| | | | 600/562 |
| 2007/0129634 A1 | 6/2007 | Hickey et al. | |
| 2008/0221453 A1 * | 9/2008 | Suri | A61B 8/12 |
| | | | 600/459 |
| 2009/0023985 A1 | 1/2009 | Ewers | |
| 2009/0072107 A1 * | 3/2009 | Wilson | A61B 90/50 |
| | | | 248/279.1 |
| 2009/0088666 A1 * | 4/2009 | Miller | A61B 10/0275 |
| | | | 600/568 |
| 2009/0253998 A1 | 10/2009 | Chen | |
| 2009/0259105 A1 | 10/2009 | Miyano et al. | |
| 2010/0056900 A1 * | 3/2010 | Whitcomb | A61B 5/055 |
| | | | 600/414 |
| 2010/0063514 A1 * | 3/2010 | Maschke | A61B 6/12 |
| | | | 606/130 |
| 2010/0198052 A1 * | 8/2010 | Jenkins | A61B 5/0555 |
| | | | 600/417 |
| 2011/0028797 A1 * | 2/2011 | Yee | A61B 5/0555 |
| | | | 600/231 |
| 2011/0319830 A1 * | 12/2011 | Peters | A61M 25/02 |
| | | | 604/180 |
| 2012/0150030 A1 * | 6/2012 | Reach, Jr. | A61B 17/1604 |
| | | | 600/427 |
| 2012/0172850 A1 * | 7/2012 | Kappel | A61B 90/50 |
| | | | 606/1 |
| 2012/0265098 A1 * | 10/2012 | McGhie | A61B 17/3403 |
| | | | 600/567 |

FOREIGN PATENT DOCUMENTS

| | | | |
|---|---|---|---|
| DE | 854100 | | 10/1952 |
| WO | WO 98/24594 | * | 6/1998 |
| WO | 2005089136 | | 9/2005 |

* cited by examiner

BIOPSY DEVICE SUPPORT OR HOLDER AND METHOD OF USE

RELATED APPLICATIONS

This application claims priority to U.S. Provisional Application No. 62/186,867 titled, "Biopsy Device Support or Holder and Method of Use," filed on Jun. 30, 2015 which is hereby incorporated by reference in its entirety.

TECHNICAL FIELD

The field of the present disclosure relates generally to medical devices. More specifically, the present disclosure relates to biopsy devices, including a support or holder configured for positioning a biopsy device.

BRIEF DESCRIPTION OF THE DRAWINGS

The embodiments disclosed herein will become more fully apparent from the following description and appended claims, taken in conjunction with the accompanying drawings. The drawings depict only typical embodiments, which embodiments will be described with additional specificity and detail in connection with the drawings in which:

DETAILED DESCRIPTION

Figure 1:
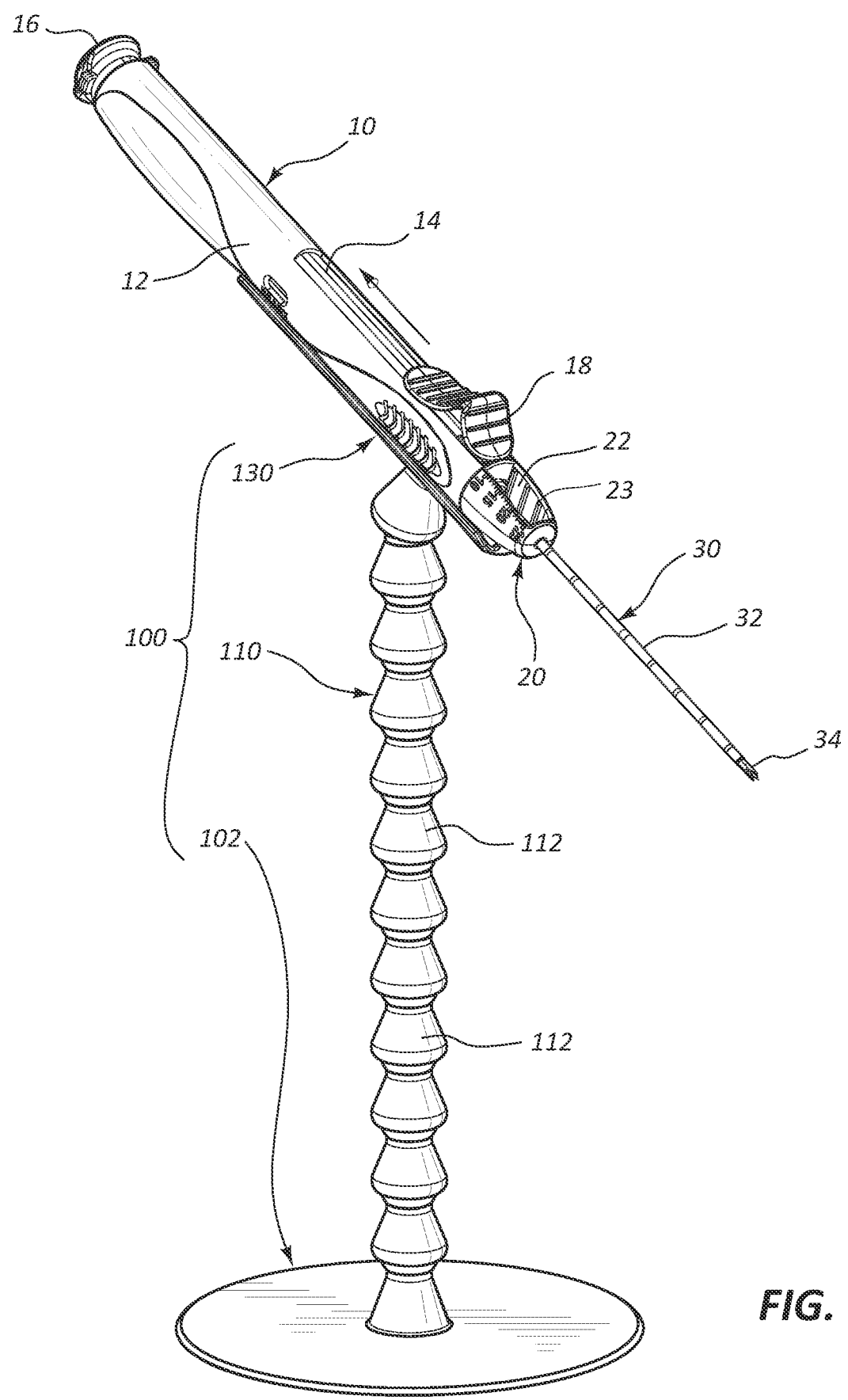
FIG. 1 is an isometric view of a support stand according to a first embodiment, including a holder at the end of the stand comprising a cradle, with a biopsy device disposed in the cradle.

Biopsy devices may be configured to retrieve tissue samples from various locations within a patient's body. For example, a biopsy device may comprise a needle assembly including cannula or other cutting members configured to sever a tissue sample. The needle assembly may be advanced to a location within the body through the skin of the patient (percutaneous access) or may be advanced through a body lumen or other structure.

Further, a biopsy device may comprise an actuation mechanism configured to displace the needle assembly such that the needle assembly severs the targeted tissue sample. Biasing mechanisms such as springs, triggers, and so forth may be configured to allow a practitioner to manipulate various components of a needle assembly through manipulating the actuation mechanism. In addition to mechanical biasing mechanisms such as springs, compressed gas (supplied for example by a compressed $CO_2$ cartridge) or other energy sources may be configured to power a biopsy device.

The biopsy device may include a mechanism configured such that, once the needle assembly is disposed adjacent the tissue to be biopsied, actuation of a single trigger may cause various components of a needle assembly to be displaced to sever a tissue sample. Biasing elements or other energy sources within the actuation mechanism may provide the force required to advance the needle assembly components, and other mechanisms may control the relative displacement of individual components of a needle assembly. A biopsy device may comprise components configured to actuate the biopsy device through transfer of kinetic energy between components, including instances where one or more components are displaced due to an impact force.

From the following descriptions, it should be understood that components of the embodiments as generally described and illustrated in the figures herein could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The phrases "connected to" and "coupled to" refer to any form of interaction between two or more entities, including mechanical, electrical, magnetic, electromagnetic, fluid, and thermal interaction. Two components may be connected or coupled to each other even though they are not in direct contact with each other. For example, two components may be coupled to each other through an intermediate component.

The directional terms "proximal" and "distal" are used herein to refer to opposite locations on a medical device. The proximal end of the device is defined as the end of the device closest to the practitioner when the device is in use by the practitioner. The distal end is the end opposite the proximal end, along the longitudinal direction of the device, or the end furthest from the practitioner.

No matter the configuration of the biopsy device, the practitioner, typically a surgeon, may need to locate the biopsy device at a desired position/orientation proximate the patient for insertion into the skin, and then once inserted, at a position for actuation of the device to sever the targeted tissue sample. The present inventors have recognized that once the biopsy device is positioned by the practitioner in a first desired position/orientation toward a target site (possibly using ultrasound or other guidance), the practitioner may desire/need to turn away from the device to confirm needle position via fluoroscopy, X-ray, CT scan, or other imaging, to verify the proper position of needle assembly, or adjust its position, prior to actuating the device.

Figure 2:
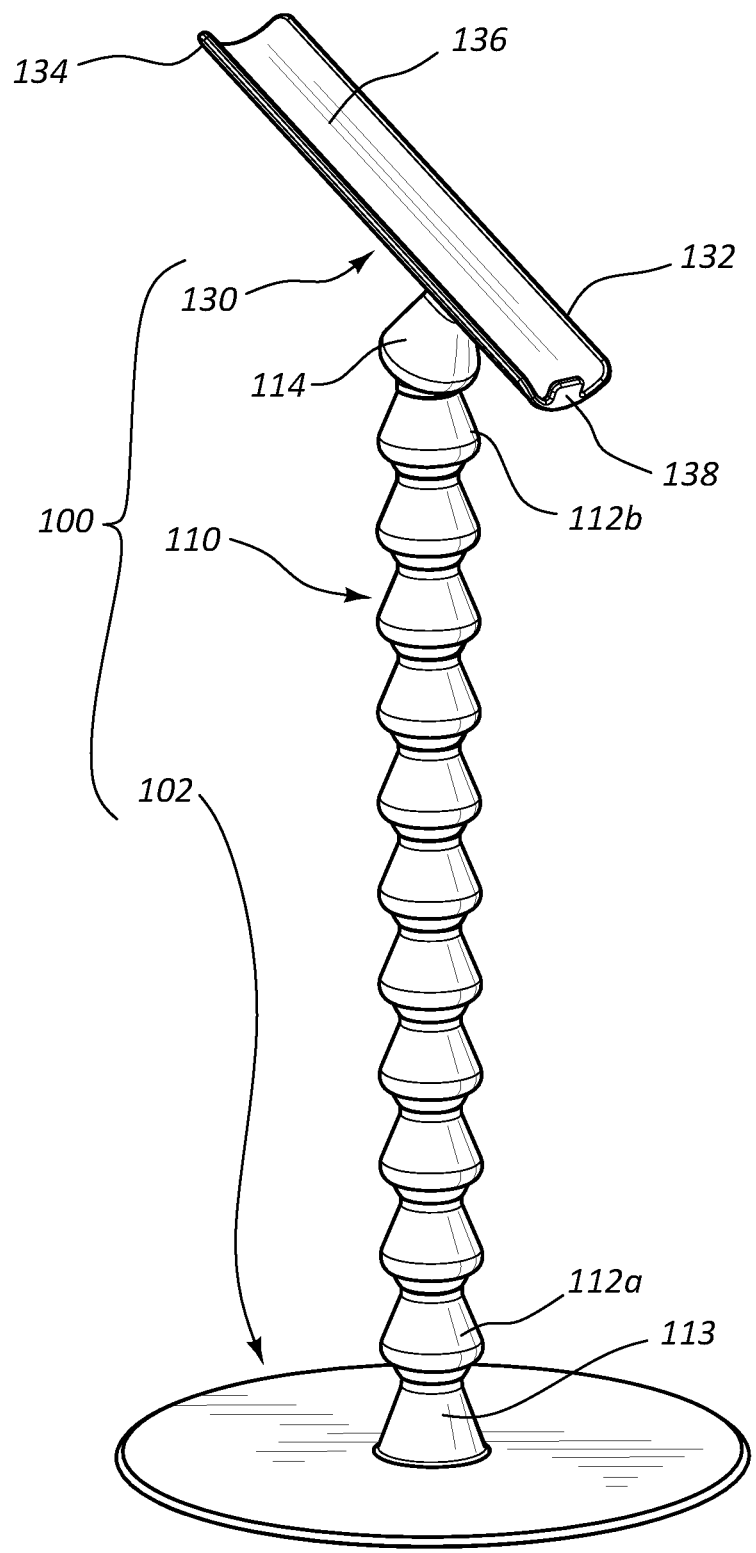
FIG. 2 is an isometric view of the support of FIG. 1 with the biopsy device removed, the support being in an upright first position.

FIG. 1 is an isometric view of a support or stand 100 according to first embodiment, including a holder section 130 at the end of the support 100 comprising, in this example a cradle, with a biopsy device 10 disposed in the holder section 130, and FIG. 2 is an isometric view of the support 100 of FIG. 1 with the biopsy device 10 removed.

The biopsy device 10 may be any suitable configuration such, for example, as the biopsy devices shown in U.S. Published Application No. 2014/0207021 hereby incorporated by reference. The biopsy device 10 shown in FIG. 1 is an impact biopsy device, including a body member 12, a priming handle disposed within the body member 12 and including an end input section 16 at the proximal end of the body member 12, a cap portion 20 at the distal end, a longitudinal input 18 (e.g., a sliding actuator or trigger) disposed for travel along a slot 14 in the body member 12, and a cutting member assembly 30 extending outwardly from the cap portion 20. The cap portion 20 includes an opening 22. In operation, the rotation of the cap portion 20 engages an internal threaded connection for adjusting stroke length to adjust or control the length of the tissue sample severed by the biopsy device 10. The cutting member assembly 30 may include a cannula 32 with trocar or stylet 34 extending out the distal end thereof. Further details of examples for the biopsy device 10 are set forth in U.S. published Application No. 2014/0207021 incorporated by reference above.

The support 100 includes a base section 102, a flexible central section 110 mounted on the base section 102, and the holder section 130 mounted onto a second end of the central section 110. The central section 110 in this embodiment is a flexible stanchion getting its flexibility via articulation of a plurality of interconnected linkage units 112, 112a, 112b, such as for example a ball and socket unit construction, arranged and extending linearly from the base section 102 to the holder section 130. In the illustrated embodiment of FIGS. 1-3, the central section 110 includes a first unit 113 attached to the base section 102, a second unit 114 attached to the holder section 130, and eleven central linkage units 112, 112a, 112b. The first unit 113 may include a ball for connection to the socket of adjacent unit 112a and the second unit 114 includes a socket for connection to adjacent unit 112b. The number and order of the linkage units 112, 112a, 112b may be modified to alternative suitable configurations. The number of central linkage units 112 may be at least one to three, constructed and arranged to provide sufficient height and overall flexibility for positioning the holder section 130 in the desired position. The length of the linkage units may be modified whereby a longer linkage unit would provide for the requirement of a fewer number of units for a given length of central section 110 but at a reduction of overall flexibility.

Other designs for the flexible center section may be employed such as a column of flexible material, for example a tube or tubular structure (hollow or non-hollow) with a flexible metal core covered with a plastic outer membrane.

The holder section 130 includes a first or proximal end 134, a second or distal end 132, a central section with a curved or concave trough 136 forming a cradle for accepting insertion of a biopsy device 10, and tab 138 at the distal end 132. The tab 138 may be sized and configured to mate/interlock with a mating section of a corresponding biopsy device. The tab 138 is optional or may merely be disposed within the opening 22 of the biopsy device 10. In one configuration, the tab 138 is keyed to fit within the opening 22 and engage between ribs 23 disposed on inner side walls of the opening 22 in the biopsy device 10.

The trough 136 may be formed in a suitable shape or cross-section to accept a desired biopsy device. The holder section 130 may be sized with a suitable longitudinal length and trough curvature/depth/diameter to adequately and stably support the biopsy device. The holder cross-section may be U-shaped, V-shaped or other suitable shape for stably holding/supporting the biopsy device. The holder section 130 may be made of a flexible material that may be flexed to provide some grasping force onto the biopsy device. The trough 136 may have an inner surface treatment or material with desired properties for engaging the biopsy device such as an adhesive or two-sided tape.

The base section 102 is shown in a round, disk-shaped configuration, but other shapes and configurations may be employed. The base section 102 may be formed from a heavy/weighted material, such as a metal, whereby the base would provide a firm base support via gravity, or merely be in the form of a plate (e.g., metal) of sufficient diameter/width to provide the desired lateral stability. Alternatively the base section 102 may incorporate magnetic material for providing a more secure attachment to a magnetically active metal surface. The bottom surface of the base section 102 may include a sticky surface treatment or an adhesive material (e.g., two-sided foam tape) or a suction surface to allow the base section 102 to be firmly secured to a table, another surface or even the patient's body or garment.

Figure 3:
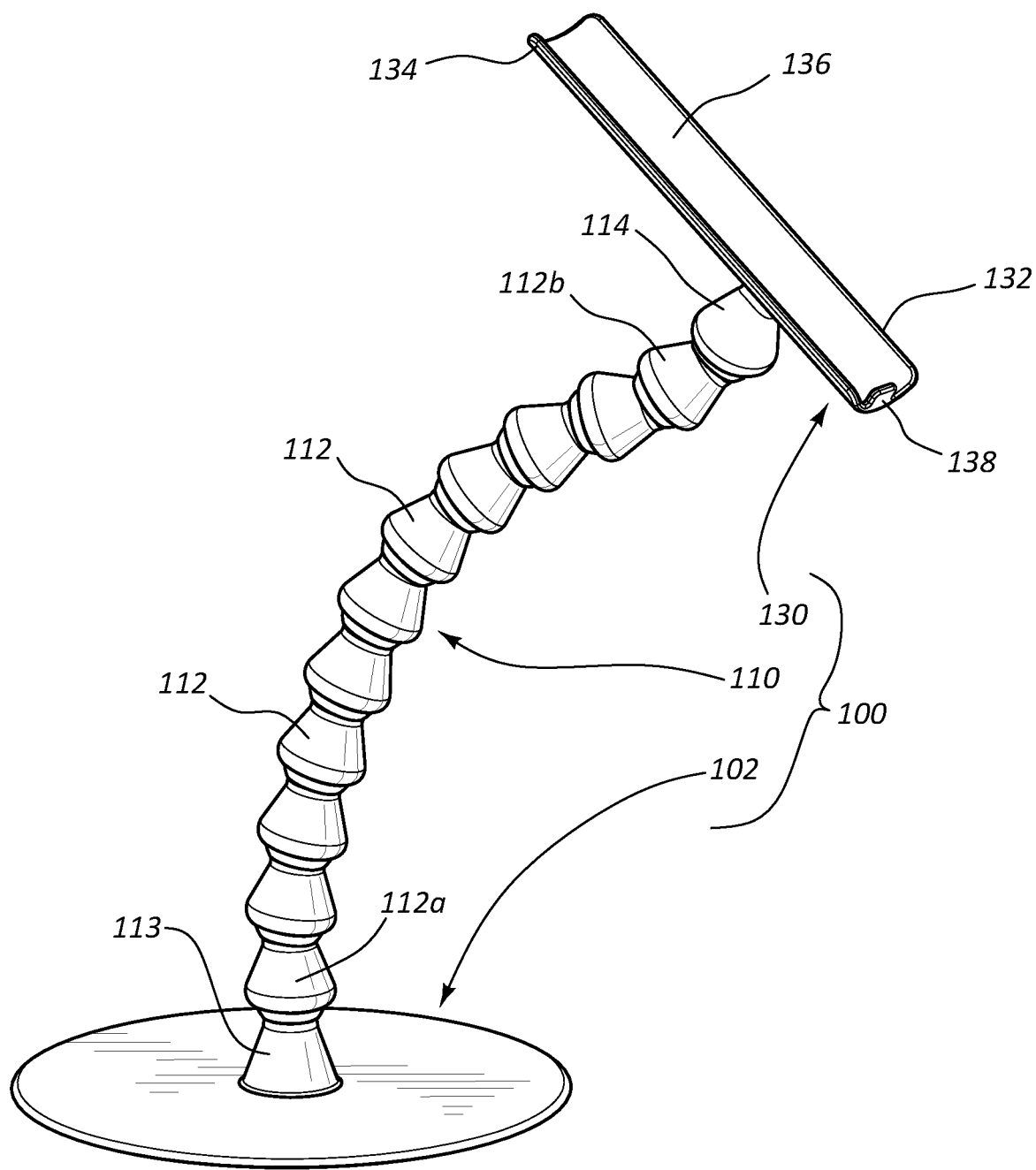
FIG. 3 is an isometric view of the support of FIG. 2 in a second position.

The support 100 is illustrated in FIGS. 1-2 in an upright or relatively straight first position. The central section 110 may be flexed or manipulated by the practitioner to a second position as shown in FIG. 3 to reposition the holder section 130 (and thus the biopsy device 10) to a desired position.

Figure 4:
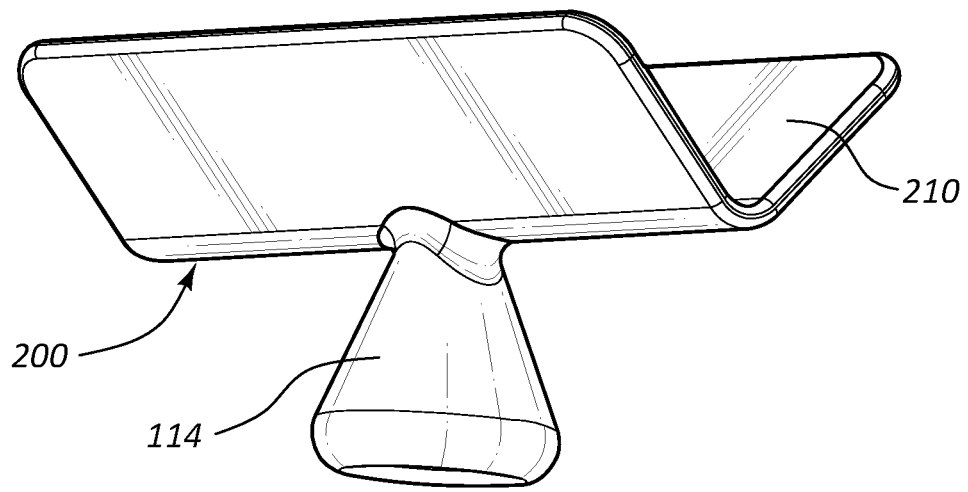
FIG. 4 is an isometric view of a first alternative holder section for the support of FIGS. 1-3.

FIG. 4 illustrates a holder 200 of an alternative configuration with a V-shaped trough 210. The holder 200 is shown with the second (linkage) unit 114 (as in the prior embodiment) attached to a bottom of the holder 200. The tab 138 of the prior embodiment has been removed. The V-shaped trough 210 may provide for a tighter fit than the U-shaped trough of the prior embodiment, such as via a snap-fit or other connection for a biopsy device (such as the biopsy device 10 shown in the prior embodiment). The snap-fit may be provided by a shoulder for engaging a corresponding lip or ridge on the body member 12 of the biopsy device 10. The trough 136 may additionally have an inner surface treatment or material with desired properties for engaging the biopsy device 10, for example an adhesive or two-side tape.

Figure 5:
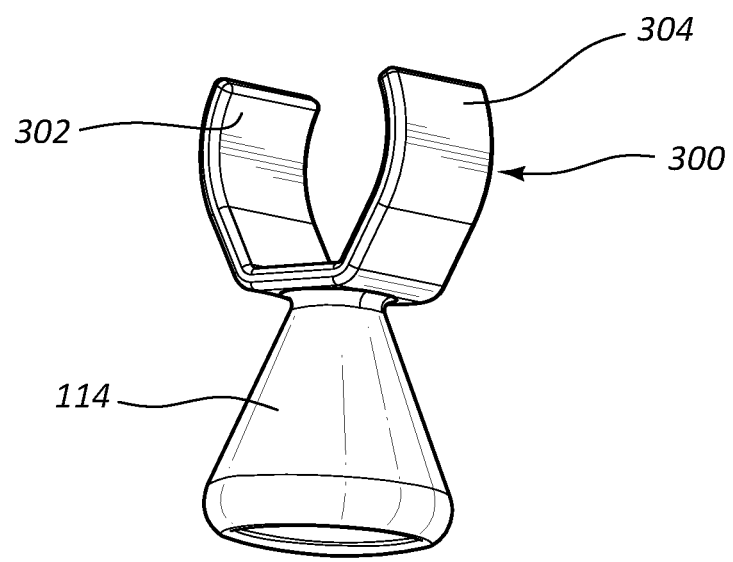
FIG. 5 is an isometric view of a second alternative holder section in the form of a clip or clasp.

FIG. 5 illustrates a holder 300 of another alternative configuration. The holder 300 includes first and second arms 302, 304 that flex to allow for insertion of a biopsy device 10 (such as the biopsy device 10 of the prior embodiment) and provide an engaging or grasping (spring) force to suitably hold the biopsy device 10 in place once inserted, such as by a snap-fit function/operation. The arms 302, 304 may be constructed of plastic, metal or other suitable material. The inner surfaces of the arms 302, 304 may additionally have an inner surface treatment or material with desired properties for engaging the biopsy device 10 thereby enhancing friction holding force and/or flexure properties.

Figure 6:
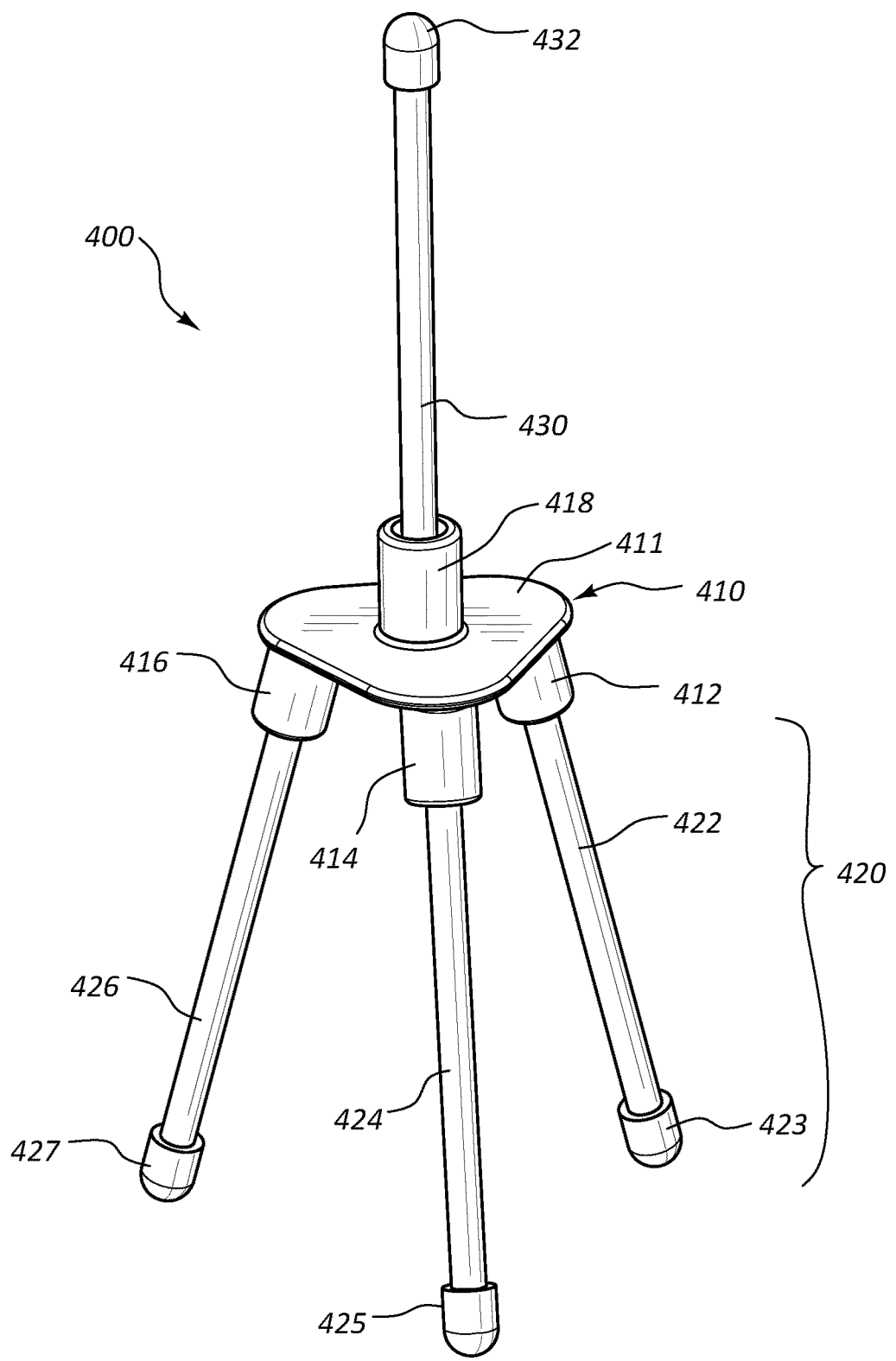
FIG. 6 is an isometric view of a support according to a second embodiment, the support being in the form of a tripod.
Figure 7:
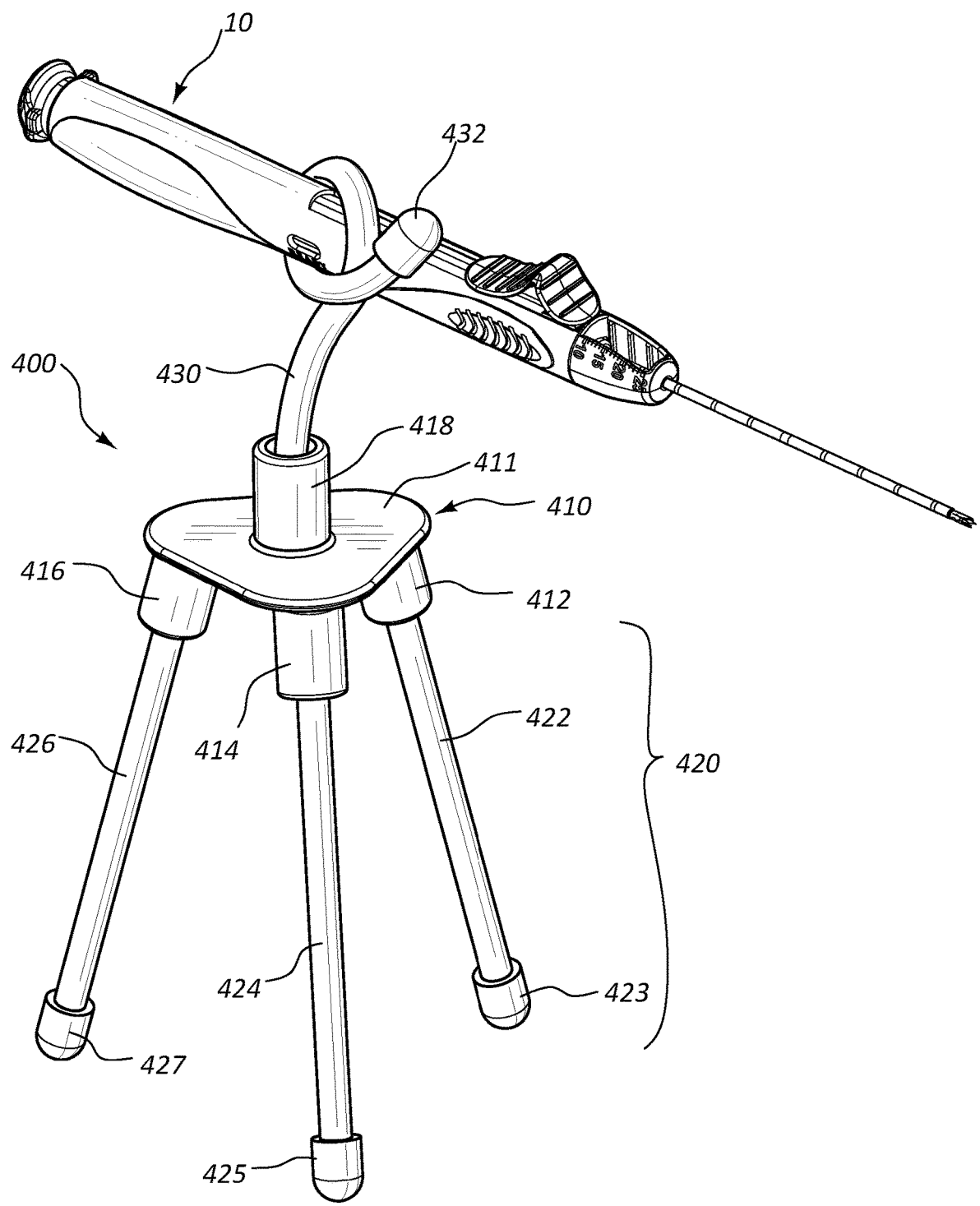
FIG. 7 is an isometric view of the support of FIG. 6 and shown holding a biopsy device.

FIGS. 6 and 7 illustrate a support 400 according to an alternate embodiment, whereby in FIG. 7 the support 400 is illustrated holding a biopsy device 10 and in FIG. 6 the support 400 is illustrated without a biopsy device. Details of the biopsy device 10 may be the same as in the previous embodiment and thus the description is not repeated for brevity. The support 400 is formed in a tripod arrangement comprising a base section 410, a leg section 420 and a holder section 430. The base section 410 includes a central portion 411, lower side connectors 412, 414, 416 and an upper side connector 418. The central portion 411 is shown with a somewhat triangular disk-shaped form, but may comprise other shapes such as round disk or spherical. The leg section 420 comprises three legs with leg 422 connected to connector 412, leg 424 connected to connector 414, and leg 426 connected to connector 416. Footings 423, 425, 427 may be placed on respective ends of the legs 422, 424, 426 for contacting a support surface. The holder section 430, which may be referred to below as an extension section or arm, is attached to the upper connector 418 of the base section and may include an end cap 432 on its distal end.

The support 400 may alternatively be formed with a different number of legs (e.g., four) or with multiple extension sections/arms.

The arm 430 and legs 422, 424, 426 are constructed to be shapeable or bendable whereby once bent into a given position/shape, the arm/leg retains the new position with reasonable stiffness so as to be able to stably support the support 400 and the biopsy device 10. The legs 422, 424, 426 may be bent into desired positions so as to locate the base section stably on a given surface or even wrapped about a given object. The arm 430 is formed with a relatively high degree of flexibility so as to allow the arm 430 to be wrapped around the biopsy device 10 as illustrated in FIG. 7, but with sufficient stiffness to allowing the biopsy device 10 to be firmly held in a desired position and orientation.

The arm 430 and the legs 422, 424, 426 may be made of any suitable material or construction such as for example a metal core coated with plastic. Moreover either the arm 430 or the legs 422-426, or both, may be formed in alternate construction such as, for example, a linkage assembly of a plurality of interconnected linkage units; a plurality of ball and socket units (see for example the central section 110 of FIG. 2); or other suitable flexible construction/structure.

In another alternative construction, the tripod-style base (namely the base section 410 and legs 422-426) of the support 400 may be substituted for the base section 102 of the FIG. 2 first embodiment. In yet another embodiment, the base section 102 may comprise a clamp device, such as a spring-loaded clamp that may be secured to a surface or object.

In operation, the holder device may be used to position or locate the biopsy device at a desired position/orientation proximate the patient for insertion into the skin, and then once inserted, at a position for actuation of the device to sever the targeted tissue sample, by the following steps:

Positioning a support device proximate the patient.
Securing the biopsy device via a holder section of the support device.
Setting an initial position of the biopsy device at a first desired position/orientation proximate a target site. If desired, employing ultrasound or other guidance to assist in the positioning.
Determining needle position via fluoroscopy, X-ray, CT scan, or other electronic imaging or detection method, to verify the proper position of the biopsy needle.
Adjusting position of the biopsy device by flexing or bending a flexible section of the support device for setting needle position of the biopsy device ready for actuation. Once in the proper position, the biopsy device may be actuated to acquire the tissue sample.

The holder section may be constructed to allow release of the biopsy device to accommodate removal of the needle from the patient.

The following claims and preceding embodiments may include descriptions of process or method steps. It should be understood that the order of the steps is not set by the order listed unless literally specified. For example, in the preceding method the step of securing the biopsy device via the holder section may occur either before or after the step of positioning the support device proximate the patient. Similarly, a user may initially advance a biopsy device into a patient to a desired location, then manipulate the support device to maintain the position of the biopsy device while positioning is confirmed, for example via x-ray. The physician may then further adjust the position of the biopsy device without necessarily manipulating the support device, then again adjust the support device to accommodate the new position of the biopsy device.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

The invention claimed is:

1. A system for positioning a biopsy device, comprising:
a biopsy device comprising a body member and a cap portion, wherein the cap portion comprises an opening; and
a support device, comprising:
a free standing base section;
a stanchion having a first end connected to the base section and a second end distal from the base section; and
a holder section disposed on or attached to the second end of the stanchion, the holder section constructed and arranged for accepting a biopsy device and holding the biopsy device in a desired orientation,
wherein the stanchion is flexible for positioning and supporting the holder section in a desired position, and
wherein the holder section comprises:
a first end;
a center section comprising an upward facing concave portion formed to accept insertion of the biopsy device; and
a second end comprising a tab, wherein the tab is keyed to fit within the opening of the cap and engage between ribs disposed on inner side walls of the cap.

2. A system according to claim 1 wherein the stanchion comprises a plurality of interconnected linkage units extending linearly from the base section to the holder section.

3. A system according to claim 1 wherein the stanchion comprises a plurality of interconnected ball and socket members extending linearly from the base section to the holder section.

4. A system according to claim 1 wherein the base section comprises a disk-shaped plate.

5. A system according to claim 1 further comprising an adhesive or tape on a bottom of the base section for securement to a support surface.

6. A system according to claim 1 wherein the stanchion is an elongated column-like structure.

7. A system according to claim 1, wherein the stanchion is connected to the base section at a central location of the base section.

8. A system according to claim 1, wherein the holder section is constructed and arranged for holding the biopsy device without gripping.

9. A system according to claim 1, wherein the holder section comprises a surface treatment configured to enhance friction between the holder section and the biopsy device.

10. A system according to claim 1, wherein the holder section comprises a ball socket for connection to the stanchion.

11. A method of positioning a biopsy device during a medical procedure on a patient, comprising the steps of:
positioning a free standing support device proximate the patient;
securing a biopsy device via a holder section of the support device,
wherein the holder section comprises:
a first end;
a center section comprising an upward facing concave portion formed to accept insertion of the biopsy device; and a second end comprising a tab, wherein the tab is keyed to fit within an opening of the biopsy device and engage between ribs disposed on inner side walls of the biopsy device,
wherein the tab is fitted into the opening of the biopsy device and engages the ribs of the biopsy device;
setting an initial position of the biopsy device at a first desired position/orientation proximate a target site in/on the patient;
determining a needle position of the biopsy device via a detection method to verify proper needle position; and
adjusting position of the biopsy device by flexing or bending a flexible section of the support device for setting needle position of the biopsy device ready for actuation.

12. A method according to claim 11 wherein the flexible section comprises a flexible central stanchion composed of a plurality of interconnected linkages, wherein adjusting position of the biopsy device comprises bending the flexible central stanchion.

13. A method of positioning a biopsy device during a medical procedure on a patient according to claim 11, wherein the holder section is configured to engage the biopsy device via a snap fit.

14. A method of positioning a biopsy device during a medical procedure on a patient according to claim 11, wherein the holder section comprises first and second flexible arms that flex to allow for insertion of the biopsy device.

15. A method of obtaining a tissue sample using a biopsy device comprising:

positioning a support device proximate the patient, the support device configured with a flexible section that may be flexed thereby allowing the practitioner to manipulate the support for re-positioning the biopsy device;
securing a biopsy device via a holder section of the support device,
wherein the holder section comprises:
a first end,
a center section comprising an upward facing concave portion formed to accept insertion of the biopsy device, and
a second end comprising a tab, wherein the tab is keyed to interlock with ribs of a mating section of the biopsy device,
wherein the tab interlocks with the ribs of the mating section of the biopsy device;
setting an initial position of the biopsy device at a first desired position/orientation proximate a target site in/on the patient;
determining a needle position of the biopsy device via an imaging detection method to verify proper needle position;
adjusting position of the biopsy device, after determining a needle position of the biopsy device via an imaging detection method to verify proper needle position, by flexing or bending a flexible section of the support device for setting needle position of the biopsy device ready for actuation; and
actuating the biopsy device to acquire a tissue sample.

\* \* \* \* \*